United States Patent [19]

Jackson

[11] 4,356,823
[45] Nov. 2, 1982

[54] SUCTION CONTROL

[76] Inventor: Richard R. Jackson, Eight Trinity Rd., Marblehead, Mass. 01945

[21] Appl. No.: 154,812

[22] Filed: May 30, 1980

[51] Int. Cl.³ .............................................. A61M 1/00
[52] U.S. Cl. ..................................... 128/276; 128/274
[58] Field of Search ............... 128/276, 274; 251/61.1, 251/44, 45

[56] References Cited

U.S. PATENT DOCUMENTS

| | | | |
|---|---|---|---|
| 2,951,496 | 9/1960 | Yarnall et al. | 137/183 |
| 3,469,582 | 9/1969 | Jackson | 128/276 |
| 3,904,168 | 9/1975 | Marocco | 251/45 |
| 3,964,484 | 6/1976 | Reynolds et al. | 128/276 |
| 4,128,227 | 12/1978 | Blomquist | 251/44 |

FOREIGN PATENT DOCUMENTS 2365157  4/1978  France ................................ 128/276

*Primary Examiner*—Richard J. Apley
*Assistant Examiner*—J. L. Kruter

[57] ABSTRACT

A medical suction control unit of the type operated by occlusion of a control port to prevent entry of atmospheric pressure into a control chamber, in which the valving element is free to move bodily between open and closed positions in response to the closing and opening of the control port, with the vacuum bleed passage, which enables air to be withdrawn from the control chamber, establishing flow around the side of the valving element. The vacuum bleed passage is shown formed by a channel in one or the other of the contacting surfaces, at the point where the valve element rests upon a surface of the housing. The valve element is shown in the form of an elastomeric disk which has sufficient structural strength to resist detrimental deformation under vacuum, and which has sufficient thickness to guide itself in its bodily movement. In one form the unit employs a plug-form member attached to the valve element and entering the intake chamber to reduce objectionable noise. The unit can be assembled by mere insertion of the free-floating valve element and snap-fit of a cap into sealing relationship with the housing, or by indenting the walls of the housing to confine the free moving valve element within the housing.

8 Claims, 8 Drawing Figures

SUCTION CONTROL

BACKGROUND OF THE INVENTION

In my U.S. Pat. No. 3,469,582 I have provided a surgical suction control unit employing a diaphragm which opens the flow passage by the simple procedure of covering a control hole, e.g. by use of the index finger of the person holding the unit. In this construction a vacuum bleed through a small passage maintains a vacuum level over the diaphragm, and holds the diaphragm in open position, when the finger closes the hole. However when the finger is removed from the control hole to allow ambient pressure to enter the control chamber, the higher pressure condition forces the diaphragm to close the flow passage.

This control unit has been effective in surgical suction devices and other applications, but, in the constructions as taught in my prior patent and as made in production, significant problems have remained.

One of the difficulties concerns the provision of an accurately sized vacuum bleed passage for connection of the control chamber to the vacuum source. If this passage is too large it wastes vacuum and the flow is noisy. If on the other hand this passage is too small, insufficient vacuum level is acquired in the control chamber and the unit does not function properly. In production, expensive molding dies having accurately fitted molding pins have been required to form such passages.

Another difficulty concerns the fact that fluids being sucked through the device often contain substances which tend to clog the vacuum bleed passage. Because of the wish to have the passage self-cleaning, the preferred form of the invention has been a tiny hole molded into the thin diaphragm, as shown in FIGS. 12-15 of my prior patent. It has however been particularly difficult to size accurately this passage through the diaphragm.

In the preferred embodiments of the past, the diaphragm, held by its periphery in the position as shown in FIGS. 12-15 of my prior patent, has been thin and flexible in order to achieve the proper flexing motion. Such a diaphragm has the disadvantage of making loud noise under certain flow conditions, for instance during partial clogging of the vacuum bleed passage or partial occlusion of the finger control port. The noise has been very high pitch, making the unit objectionable.

Still other problems have concerned the time and expense of manufacture of the unit. In present commercial forms the parts must be clamped in a jig and the elements are then cemented together.

Purposes of the present invention are to overcome these disadvantages and to provide an improved suction control unit.

SUMMARY OF THE INVENTION

The invention, in its various features, relates to a suction control unit comprising a housing, with a suction connection to a source of vacuum and an intake connection through which fluid is to be evacuated by the unit, the unit having a movable valving element exposed to a control chamber, means establishing a vacuum bleed passage between the suction side of the instrument and said control chamber and an occludable control port permitting entry of atmospheric pressure to said control chamber when the port is opened and preventing entry of atmospheric pressure when the control port is occluded.

According to the invention the valving element comprises a relatively thick valving element disposed within the control chamber and free to move bodily between open and closed positions in response to varying pressure determined by the closing and opening of the control port, the vacuum bleed passage enabling air to be withdrawn from the control chamber around the side of the valving element.

In preferred embodiments a surface portion of the valve element rests in contact upon a corresponding surface of the interior of the housing, and the vacuum bleed passage is defined by a channel formed in at least one of the contacting surfaces, this channel being in the form of a notch of molded form in the periphery of the valve element or in a valve element-supporting peripheral ledge of the housing.

For noise suppression in which a central chamber is in communication with the intake connection of the unit and an annular chamber surrounds the central chamber, separated therefrom by an annular wall, with the annular chamber connected to the vacuum connection of the unit, a plug-form member is employed depending from the valve element and aligned to enter the central chamber when the valve element is in its closed position, the unit constructed to enable the plug-form member to be withdrawn from the central chamber by movement of the valve element upon the occlusion of the control port.

For simplified construction of the unit a cover member defining the control port is snap fitted about walls of the housing in sealing relationship therewith or the housing defines a control port of a size substantially corresponding to the size of the valve element, the size being sufficiently small to enable occlusion of the port by the finger of the operator and inwardly protruding formations of the housing walls comprise a retainer means for the valve element.

In preferred embodiments the valve element is of circular disk form, comprised of rubber and has a thickness of the order of 1.5 millimeters.

DRAWINGS

PREFERRED EMBODIMENTS

Figure 1:
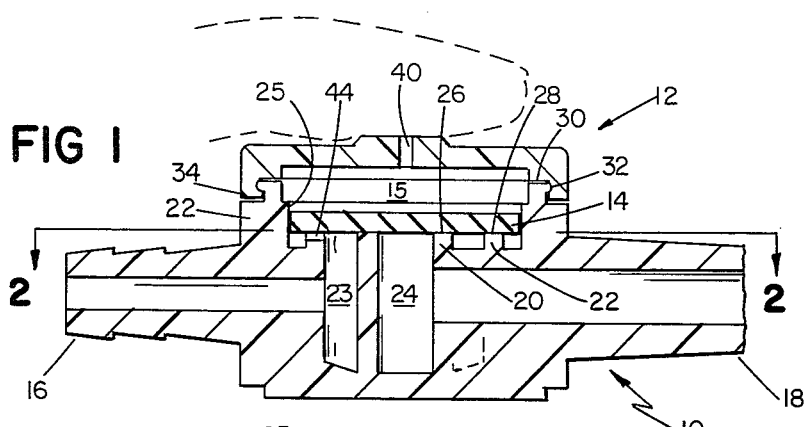
FIG. 1 is a vertical cross-sectional view of a first embodiment.

Referring to FIG. 1 the control unit comprises a body member 10, a cap member 12 and a free-floating valve element 14, with the control chamber 15 defined between the cap member and valve element. The body member 10 has a suction connector 16 for connection to a vacuum source and an intake connector 18 for connection to the system to be evacuated by the unit. The body member also defines an inner annular separator wall 20 spaced inwardly from outer wall 22. The suction connector 16 is connected to the annular space 23 between walls 20 and 22 while the intake connector 18 projects across space 23 and connects to the inner space 24 defined within the inner annular wall 20. At a height corresponding with the top edge 26 of the inner annular wall 20, an inner ledge 28 is defined by the outer wall 22. An extension 25 of the outer wall extends upwardly from ledge 28 to upper edge 30 and a securing rim 32 protrudes outwardly from the edge 30. The dome or cap member 12, formed of resilient material, e.g., pvc, has a dependent rim 34 which resiliently snaps around the rim 32 and forces the cap member into sealing relationship with edge 30 of the outer wall. An atmospheric port 40 is formed through the substance of cap member 12 while the outer surface of the cap member is shaped to be engaged by the finger of the operator as suggested in dotted lines.

The free-floating valve element 14 is disposed within the space above ledge 28. It comprises a circular member of silicone rubber of medium durometor and thickness of about 1½ millimeters. Its diameter is less than the diameter of the upper extension 25 of outer wall, enabling free, non-sealed and non-restrained movement relative to outer wall 25. The valve element 14 is sized to have its outer margin rest upon ledge 28, while inward portion of the element bears upon edge 26 of the inner wall. The valve element has structural stability to remain in position when exposed to full vacuum at outer annular space 23 and while exposed along its top surface to atmospheric pressure. The structural stability of the element is also such that element 14 can guide itself along the annular wall in axial motion in response to changing pressure conditions.

Figure 1A:
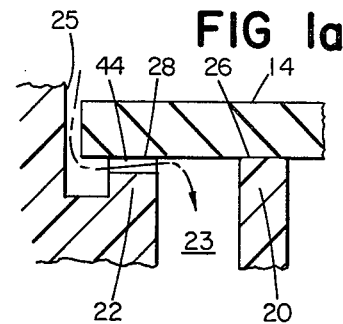
FIG. 1a is a magnified detail view of the vacuum bleed passage of FIG. 1.
Figure 2:
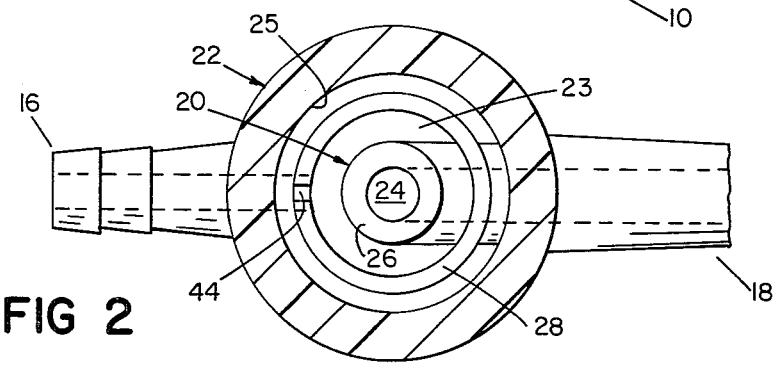
FIG. 2 is a horizontal cross-sectional view taken on line 2—2 of FIG. 1.

A notch 44 (see FIGS. 1a and 2) molded into the ledge 28 of the outer wall serves as a vacuum bleed passage between the annular vacuum space 23 and the control chamber 15, with air being drawn from the control chamber past the free peripheral edge of the valve element 14 through the notch-form passage 44 and into the vacuum connector 16.

The valve element 14 is free to move axially back and forth within the confines of the extension 25 of the outer wall in response to pressure conditions. During operation, with the operator's finger off of the outer control port 40, atmospheric pressure, entering through the control port 40, fills the control chamber 15 and bears downwardly upon the upper surface of the disc-form valve element 14. Simultaneously suction applied to connector 16 applies reduced pressure to the annular area of the valve element corresponding to the annular chamber 20. This draws the valve element tightly against the upper edge 26 of inner wall 20, forming a seal and preventing flow between connectors 18 and 16.

When, however, the operator's finger is placed over the control port 40 as suggested by the dotted lines, atmospheric pressure is prevented from entering the control chamber 15. Rapidly the vacuum, acting through the bleed passage 44 at the ledge, draws air from the control chamber 15 to produce a vacuum condition in control chamber 15. Under this condition the atmospheric pressure entering through connector 18 into inner chamber 24 is successful to push valve element 14 upwardly, to establish flow from connector 18 through chamber 24, over edge 26 of inner annular wall 20, thence to annular space 23 and to suction connector 16.

A number of advantages are obtained by this construction. The vacuum bleed passage 44, being molded as a notch in a surface is inexpensive to fabricate in the mold, eliminating the need for molding pins and the expensive mold construction that must be employed with such pins.

The free floating valve element 14, due to its relatively great thickness and mass causes any vibration that may occur to be of low frequency and amplitude, greatly reducing the noise of the unit.

During construction, the valve element 14 is merely loosely dropped into the body and the cap 12 is snapped into place on the top of the unit to complete the manufacture.

Figure 3:
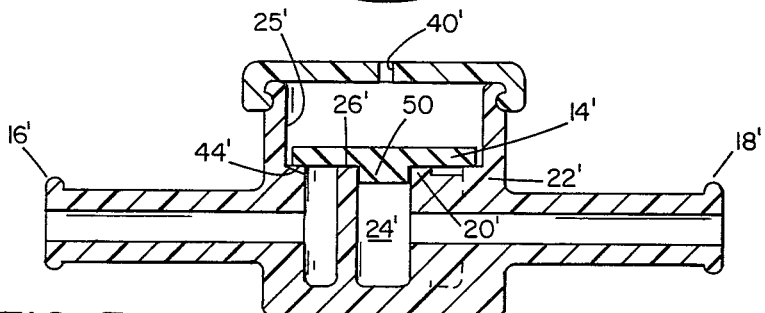
FIG. 3 is a vertical cross-sectional view similar to FIG. 1 showing an embodiment which is even more silent in operation.

The variation of FIG. 3 is constructed to reduce noise even further. Central formation 50 formed integrally with valve element 14' fits slidingly with the wall 20 that defines the central chamber 24. Also the outer wall 25' is of extended height to enable the movement of valve element 14' over a wider range than in FIG. 1 to enable the plug 50 to be withdrawn from central chamber 24. In operation, when operator's finger is not occluding the control port 40 the atmospheric pressure causes valve element 14' to seal against edge 26 of inner annular wall 20, disposing inner plug member 50 within central chamber 24.

During operation, when the operator's finger is placed over the control port 40 to change the pressure conditions, no significant flow occurs through the instrument until valve element 14' moves sufficiently to withdraw the central plug member 50 from the central cavity. At this time, when heavy flow is allowed to begin, the surrounding body of the valve element 14' has been withdrawn a substantial distance from the annular sealing surface 28, hence, because of the wide space between parts, there is virtually no opportunity for noise-producing vibrations to be established.

Figure 4:
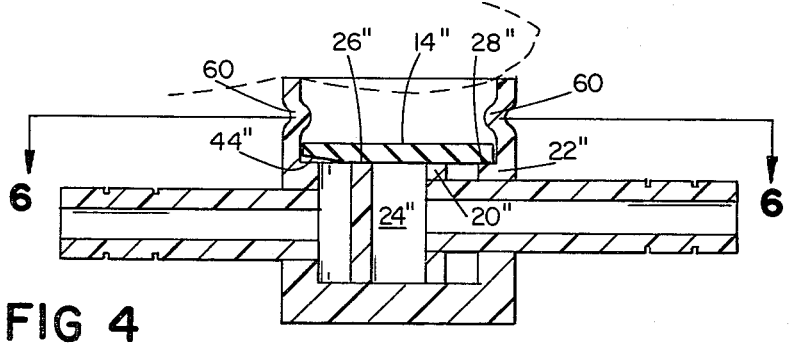
FIG. 4 is a vertical cross sectional view of an embodiment of simplified two piece construction.
Figure 4A:
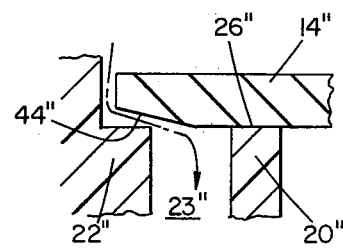
FIG. 4a is a magnified detail view of the vacuum bleed passage of FIG. 4.
Figure 6:
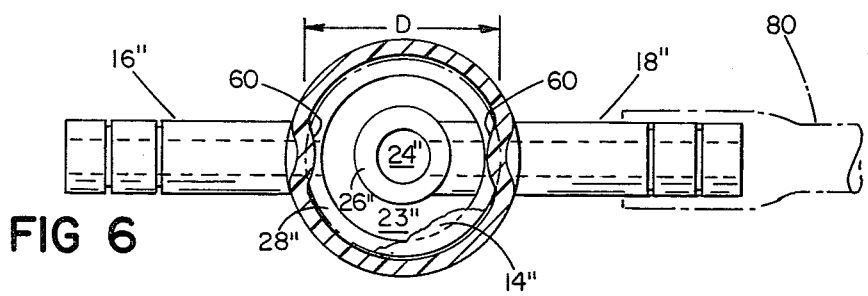
FIG. 6 is a horizontal cross-sectional view taken on line 6—6 of FIG. 4.
Figure 5:
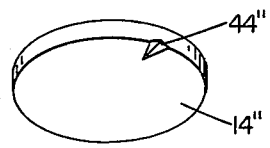
FIG. 5 is a perspective view of the valve element employed in the embodiment of FIG. 4.

Referring to FIGS. 4-6, in this embodiment the valve element 14" has a notch 44' formed in its periphery for establishing the restricted vacuum bleed passage between the control chamber and the vacuum chamber of the instrument. In this case the ledge 28' upon which the valve element seats has no notch.

Also in this embodiment, the diameter D of the outer wall, FIG. 6, is of the order of a centimeter, permitting the finger of the operator to entirely occlude the control chamber, hence there is no need for a cap. In this case the top edge of the outer wall defines the control port.

In construction of this unit, the valve element 14" is introduced into the body and then the upper wall is crimped to form inwardly protruding ears 60 which confine the valve element within the unit. In FIG. 6 a suction tube 80 is connected to the unit. This suction tube leads to a system to be evacuated that is so constructed that only air passes through tube 80 and hence the operator's finger is not exposed to contaminating liquids. In other instances the operator's finger is protected by a glove in the usual way.

What is claimed is:

1. In a medical suction control unit comprising a housing, a suction connection to a source of vacuum and an intake connection through which fluid is to be evacuated by the unit, the unit having a movable valving element exposed to a control chamber, means establishing a vacuum bleed passage between the suction side of the instrument and said control chamber and an occludable control port permitting entry of atmospheric pressure to said control chamber when the port is open and preventing entry of atmospheric pressure when the control port is occluded, the improvement wherein said valving element comprises a relatively thick free-floating, shape retentive valving element resistant to bodily deformation under vacuum disposed within the control chamber and free to move in bodily reciprocating motion between open and closed positions in response to varying pressure determined by the closing and opening of said control port, in closed position a surface portion of said valve element resting in contact upon a corresponding surface of the interior of said housing, said vacuum bleed passage defined by a channel formed in at least one of the contacting surfaces of said valve element and said housing, said vacuum bleed passage enabling air to be withdrawn from said control chamber around the side of said valving element.

2. The suction control unit of claim 1 wherein said channel is in the form of a notch of molded form in the periphery of said valve element.

3. The vacuum control unit of claim 1 wherein walls of said housing define a control port of a size substantially corresponding to the size of said valve element, said size being sufficiently small to enable occlusion of said port by the finger of the operator.

4. The vacuum control unit of claim 3 including inwardly protruding formations of said housing wall, said protrusions comprising a retainer means for said valve element.

5. In a medical suction control unit comprising a housing, a suction connection to a source of vacuum and an intake connection through which fluid is to be evacuated by the unit, the unit having a movable valving element exposed to a control chamber, means establishing a vacuum bleed passage between the suction side of the instrument and said control chamber and an occludable control port permitting entry of atmospheric pressure to said control chamber when the port is open and preventing entry of atmospheric pressure when the control port is occluded, the improvement wherein said valving element comprises a relatively thick free-floating, shape retentive valving element resistant to bodily deformation under vacuum disposed within the control chamber and free to move in bodily reciprocating motion between open and closed positions in response to varying pressure determined by the closing and opening of said control port, a surface portion of said valve element resting in contact upon a corresponding surface of the interior of said housing, said vacuum bleed passage defined by a channel, said channel in the form of a notch in a valve element-supporting peripheral ledge of said housing, said vacuum bleed passage enabling air to be withdrawn from said control chamber around the side of said valving element.

6. In a medical suction control unit comprising a housing, a suction connection to a source of vacuum and an intake connection through which fluid is to be evacuated by the unit, the unit having a movable valving element exposed to a control chamber, means establishing a vacuum bleed passage between the suction side of the instrument and said control chamber and an occludable control port permitting entry of atmospheric pressure to said control chamber when the port is open and preventing entry of atmospheric pressure when the control port is occluded, the improvement wherein said valving element comprises a relatively thick valving element disposed within the control chamber and free to move bodily between open and closed positions in response to varying pressure determined by the closing and opening of said control port, in closed position a surface portion of said valve element resting in contact upon a corresponding surface of the interior of said housing, said vacuum bleed passage defined by a channel formed in at least one of the contacting surfaces of said valve element and said housing, said vacuum bleed passage enabling air to be withdrawn from said control chamber around the side of said valving element, and wherein said housing defines a central chamber in communication with the intake connection of the unit and an annular chamber surrounds said central chamber, separated therefrom by an annular wall, said annular chamber connected to the vacuum connection of the unit, and a plug-form member depending from said valve element and aligned to enter said central chamber when said valve element is in its closed position, the unit constructed to enable said plug-form member to be withdrawn from said central chamber by movement of said valve element upon the occlusion of said control port.

7. In a medical suction control unit comprising a housing, a suction connection to a source of vacuum and an intake connection through which fluid is to be evacuated by the unit, the unit having a movable valving element exposed to a control chamber, means establishing a vacuum bleed passage between the suction side of the instrument and said control chamber and an occludable control port permitting entry of atmospheric pressure to said control chamber when the port is open and preventing entry of atmospheric pressure when the control port is occluded, the improvement wherein said valving element comprises a relatively thick free-floating, shape retentive valving element resistant to bodily deformation under vacuum disposed within the control chamber and free to move in bodily reciprocating motion between open and closed positions in response to varying pressure determined by the closing and opening of said control port, said vacuum bleed passage enabling air to be withdrawn from said control chamber around the side of said valving element and said unit includes a cover member defining said control port, said cover member snap fit about walls of said housing in sealing relationship therewith.

8. The vacuum control unit of claim 1, 6 or 3 wherein said valve element is of circular disc form, comprised of rubber and has a thickness of the order of 1.5 millimeters.

* * * * *